US008663626B2

(12) United States Patent
Levenberg et al.

(10) Patent No.: US 8,663,626 B2
(45) Date of Patent: Mar. 4, 2014

(54) VASCULARIZED ISLETS AND METHODS OF PRODUCING SAME

(75) Inventors: Shulamit Levenberg, Moreshet (IL); Keren Francis, Kiryat-Tivon (IL)

(73) Assignee: Technion Research & Development Foundation Limited, Haifa (IL)

( * ) Notice: Subject to any disclaimer, the term of this patent is extended or adjusted under 35 U.S.C. 154(b) by 600 days.

(21) Appl. No.: 12/450,112

(22) PCT Filed: Mar. 12, 2008

(86) PCT No.: PCT/IL2008/000337
§ 371 (c)(1),
(2), (4) Date: Dec. 2, 2009

(87) PCT Pub. No.: WO2008/111064
PCT Pub. Date: Sep. 18, 2008

(65) Prior Publication Data
US 2010/0092433 A1  Apr. 15, 2010

Related U.S. Application Data

(60) Provisional application No. 60/906,223, filed on Mar. 12, 2007.

(51) Int. Cl.
*A01N 63/00* (2006.01)
(52) U.S. Cl.
USPC ........................................................ 424/93.7
(58) Field of Classification Search
None
See application file for complete search history.

(56) References Cited

U.S. PATENT DOCUMENTS

2003/0113302 A1   6/2003   Revazova et al.

FOREIGN PATENT DOCUMENTS

WO    WO 02/078439    10/2002
WO    WO 2008/111064   9/2008

OTHER PUBLICATIONS

Linn et al., FASEB Journal, 2003, vol. 17, p. 881-883.*
Johansson et al., American Journal of Transplantation, 2005, vol. 5, p. 2632-2639.*
Kellar et al., Circulation, 2001, vol. 104, p. 2063-2068.*
Levenberg et al., Nature Biotechnology, 2005, vol. 23, No. 7, p. 879-884.*
Linn et al., Cell transplantation, 2003, vol. 12, No. 7, pp. 769-778, Abstract Only.*
NPL search results, 2 pages of PDF, Sep. 17, 2013.*
Office Action Dated Aug. 30, 2011 From the Israeli Patent Office Re. Application No. 200839 and Its Translation Into Englilsh.
International Preliminary Report on Patentability Dated Sep. 24, 2009 From the International Bureau of WIPO Re.: Application No. PCT/IL2008/000337.
International Search Report and the Written Opinion Dated Jul. 18, 2008 From the International Searching Authority Re.: Application No. PCT/IL2008/000337.
Communication Pursuant to Article 94(3) EPC Dated Sep. 20, 2012 From the European Patent Office Re. Application No. 08719962.6.
Chung et al. "Human Embryonic Stem Cell Lines Generated Without Embryo Destruction", Cell Stem Cell, 2(2): 113-117, Feb. 7, 2008.
Office Action Dated Jun. 27, 2013 From the Israeli Patent Office Re. Application No. 200839 and Its Translation Into English.

* cited by examiner

*Primary Examiner* — Kade Ariani

(57) ABSTRACT

An isolated composition of matter is provided comprising a heterogeneous population of cells seeded on a surface of a scaffold, wherein the heterogeneous population of cells comprises at least one pancreatic islet, endothelial cells and fibroblast cells. Methods of generating same and uses thereof are also provided.

3 Claims, 5 Drawing Sheets
(4 of 5 Drawing Sheet(s) Filed in Color)

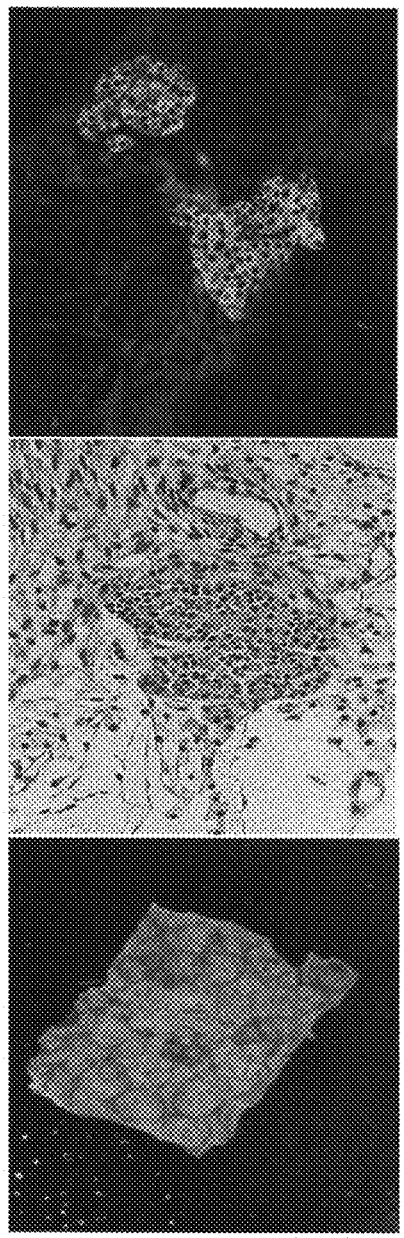

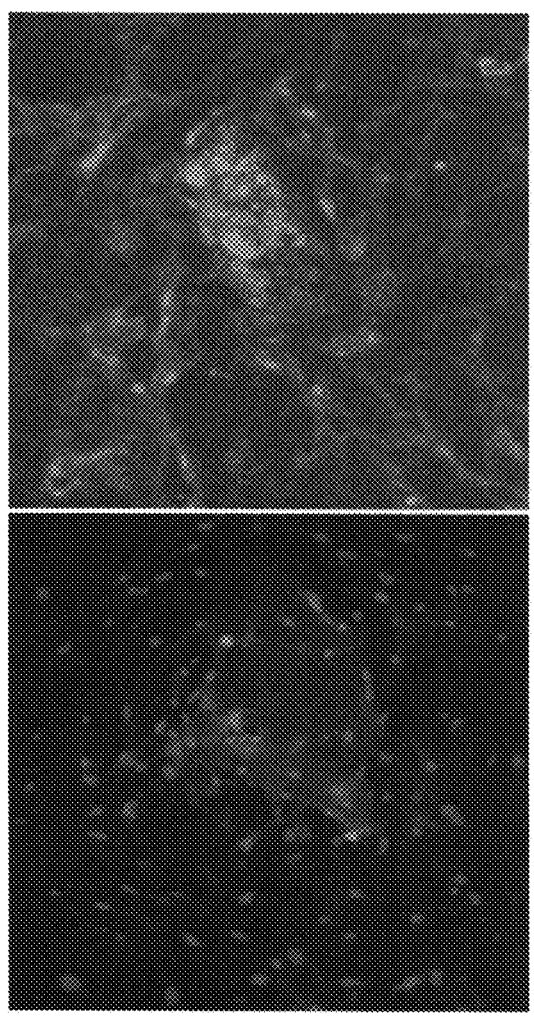

ial Filing Date of Mar. 12, 2008, which claims priority
VASCULARIZED ISLETS AND METHODS OF PRODUCING SAME

RELATED APPLICATIONS

This application is a National Phase Application of PCT Patent Application No. PCT/IL2008/000337 having International Filing Date of Mar. 12, 2008, which claims priority from U.S. Provisional Patent Application No. 60/906,223, filed on Mar. 12, 2007. The contents of the above Applications are all incorporated herein by reference.

FIELD AND BACKGROUND OF THE INVENTION

The present invention relates to a scaffold comprising vascularized islets which may be transplanted into the body for the treatment of diabetes.

Insulin-dependent diabetes mellitus (IDDM) is a chronic inflammatory disease in which there is autoimmune-mediated organ-specific destruction of the insulin-producing beta cells in the pancreatic islets of Langerhans. This causes glucose homeostasis abnormalities resulting in metabolic complications that are frequently debilitating and life threatening.

Replacing the beta cells has been a therapeutic goal for decades since it is believed that this treatment would prevent the morbidity and mortality associated with DM. Islet transplantation is considered a potentially curative treatment for type 1 diabetes [Shapiro A. M. Diabetes Technol Ther. 2000 Autumn; 2(3):449-52]. However, this protocol is yet to be successful. One of the most likely reasons for the poor success thus far in islet cell transplantation is that these tissue grafts must establish new vasculature from the host to survive.

Native islets in the pancreas have a rich vascular structure thought to provide efficient delivery of oxygen and nutrients to islet cells and ensure rapid dispersal of pancreatic hormones to the circulation [Jansson, L. & Carlsson, P. O. Diabetologia 45, 749-763 (2002); Menger, M. D., Yamauchi, J. & Vollmar, B. World J Surg 25, 509-515 (2001)]. In contrast, isolated islets are severed from their native vascular network. Traditionally, both in experimental and clinical islet transplantation, the islets are cultured for several days between isolation and transplantation. The endothelial cells that remain in the islets following islet isolation, the intra-islet endothelial cells, have been sparsely studied and shown to be lost following 7 days of islet culture [Mendola, J. F. et al. Transplant Proc 26, 689-691 (1994); Parr, E. L., Bowen, K. M. & Lafferty, K. J. Transplantation 30, 135-141 (1980)]. Therefore, after implantation, the survival and function of islet grafts must depend on the reestablishment of new vessels within the grafts to derive blood flow from the host vascular system [Jansson, L. & Carlsson, P. O. Diabetologia 45, 749-763 (2002); Menger, M. D., Yamauchi, J. & Vollmar, B. World J Surg 25, 509-515 (2001)]. During the time required for such revascularization, there is a much-increased susceptibility to loss from ischemic injury (e.g., lack of oxygen or nutrients). Therefore, rapid and adequate islet revascularization may be crucial for the survival and function of transplanted islets [Zhang N et al., Am J Transplant 3, 1230-1241 (2003)].

There have been attempts to improve the vascularization of transplanted pancreatic islets using acidic fibroblast growth factor. When syngeneic rat pancreas islets were transplanted into a kidney in the presence of this growth factor, the result was that more capillaries served the beta-cell-containing islet medulla, and a greater number of beta cells produced insulin [Jansson, L. & Carlsson, P. O. Diabetologia 45, 749-763 (2002); Menger, M. D., Yamauchi, J. & Vollmar, B. World J Surg 25, 509-515 (2001)].

U.S. Patent Application No. 20050048040 teaches a method for enhancing vascularization of islets by increasing the quantity and/or quality of endothelial cells residing within. U.S. Patent Application No. 20050048040 does not teach use of scaffolds to promote formation of 3D vascular structures thereby allowing ex vivo regulation of such structures.

U.S. Patent Application No. 20030113302 also teaches a method for enhancing vascularization of islets by contact thereof with endothelial cells in the presence or absence of a scaffold. U.S. Patent Application No. 20030113302 does not teach transplantation of preformed vascular beds or other vascular structures, either separately or within the scaffold.

It is estimated that less than 30% of islet mass becomes stably engrafted, despite the administration of a large quantity of islets per diabetic recipient [Boker A. et al., World J Surg 25, 481-486 (2001)]. Given a limited supply of cadaveric donors and the prevalence of type 1 diabetes, there is a widely recognized need for, and it would be highly advantageous to have, methods of preventing the loss of islet mass in the immediate post transplant period.

SUMMARY OF THE INVENTION

According to one aspect of the present invention there is provided an isolated composition of matter comprising a heterogeneous population of cells seeded on a scaffold, wherein the heterogeneous population of cells comprises at least one pancreatic islet, endothelial cells and fibroblast cells.

According to another aspect of the present invention there is provided an isolated composition of matter comprising a vascularized islet seeded on a scaffold, the vascularized islet comprising B cells, wherein a vasculature of the vascularized islet is sufficient for survival for at least three weeks of the B cells.

According to yet another aspect of the present invention there is provided an isolated composition of matter comprising a heterogeneous population of cells seeded on a porous scaffold, wherein the heterogeneous population of cells comprises at least one pancreatic islet and endothelial cells and whereas a pore of the porous scaffold comprises a minimal average pore diameter of about 300 μm.

According to still another aspect of the present invention there is provided a method of ex vivo vascularizing an islet, the method comprising culturing a scaffold-supported islet and endothelial cells under conditions which allow the formation of at least one 3D endothelial structure within the scaffold, thereby ex vivo vascularizing the islet.

According to an additional aspect of the present invention there is provided a method of treating diabetes in a subject, comprising transplanting a therapeutically effective amount of the isolated composition of matter of the present invention into the subject, thereby treating diabetes.

According to yet an additional aspect of the present invention there is provided a pharmaceutical composition comprising as an active agent the isolated composition of matter of the present invention, and a pharmaceutically acceptable carrier.

According to still an additional aspect of the present invention there is provided a use of the isolated composition of matter of the present invention for the manufacture of a medicament identified for the treatment of diabetes.

According to further features in preferred embodiments of the invention described below, the scaffold is a porous scaffold.

According to still further features in the described preferred embodiments, a pore of the porous scaffold comprises a minimal average pore diameter of about 300 μm.

According to still further features in the described preferred embodiments, a pore of the porous scaffold comprises a maximal average pore diameter of about 800 μm.

According to still further features in the described preferred embodiments, the scaffold comprises poly(L-lactic acid) and poly(lactic acid-co-glycolic acid).

According to still further features in the described preferred embodiments, the scaffold comprises a 50:50 mixture of poly(L-lactic acid) and poly(lactic acid-co-glycolic acid).

According to still further features in the described preferred embodiments, the scaffold is biodegradable.

According to still further features in the described preferred embodiments, the scaffold is non-biodegradable.

According to still further features in the described preferred embodiments, the scaffold comprises a material selected from the group consisting of collagen-GAG, collagen, fibrin, PLA, PGA, PLA-PGA co-polymer, poly(anhydride), poly(hydroxy acid), poly(ortho ester), poly(propylfumerate), poly(caprolactone), polyamide, polyamino acid, polyacetal, biodegradable polycyanoacrylate, biodegradable polyurethane and polysaccharide, polypyrrole, polyaniline, polythiophene, polystyrene, polyester, non-biodegradable polyurethane, polyurea, poly(ethylene vinyl acetate), polypropylene, polymethacrylate, polyethylene, polycarbonate and poly(ethylene oxide).

According to still further features in the described preferred embodiments, the scaffold further comprises at least one agent.

According to still further features in the described preferred embodiments, the at least one agent is for promoting cell adhesion, colonization, proliferation, differentiation, extravasation and/or migration.

According to still further features in the described preferred embodiments, the at least one agent is an amino acid, a small molecule chemical, a peptide, a polypeptide, a protein, a DNA, an RNA, a lipid and/or a proteoglycan.

According to still further features in the described preferred embodiments, the protein is selected from the group consisting of an extracellular matrix protein, a cell adhesion protein, a growth factor, a cytokine, a hormone, a protease and a protease substrate.

According to still further features in the described preferred embodiments, the cell adhesion protein is fibronectin.

According to still further features in the described preferred embodiments, the at least one agent is attached to, embedded or impregnated in the scaffold.

According to still further features in the described preferred embodiments, the scaffold is coated with a gel.

According to still further features in the described preferred embodiments, the gel is selected from the group consisting of a collagen gel, an alginate, an agar, a growth factor-reduced Matrigel, and MATRIGEL™.

According to still further features in the described preferred embodiments, the fibroblasts are mouse embryonic fibroblasts.

According to still further features in the described preferred embodiments, the fibroblasts are human embryonic fibroblasts.

According to still further features in the described preferred embodiments, the at least one islet is an intact islet.

According to still further features in the described preferred embodiments, the at least one islet is a non-intact islet.

According to still further features in the described preferred embodiments, the endothelial cells are embryonic stem cell-derived endothelial cells or umbilical vein endothelial cells.

According to still further features in the described preferred embodiments, the embryonic stem cell-derived endothelial cells are mammalian stem cell derived endothelial cells.

According to still further features in the described preferred embodiments, the mammalian embryonic stem cell-derived endothelial cells are human stem cell derived endothelial cells.

According to still further features in the described preferred embodiments, the umbilical vein endothelial cells are human or mouse umbilical vein endothelial cells.

According to still further features in the described preferred embodiments, the endothelial cells are mammalian aortic endothelial cells.

According to still further features in the described preferred embodiments, the endothelial cells form part of a 3D endothelial structure.

According to still further features in the described preferred embodiments, the 3D endothelial structure comprises a lumen.

According to still further features in the described preferred embodiments, the conditions comprise an ex vivo culturing period of at least 1 week.

According to still further features in the described preferred embodiments, the conditions comprise co-culturing fibroblast cells on the scaffold.

The present invention successfully addresses the shortcomings of the presently known configurations by providing pre-vascularized islets for transplant into diabetic subjects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

The patent or application file contains at least one drawing executed in color. Copies of this patent or patent application publication with color drawing(s) will be provided by the Office upon request and payment of the necessary fee.

Figures 3A, 3B, 3C:
Figures 3D, 3E, 3F:
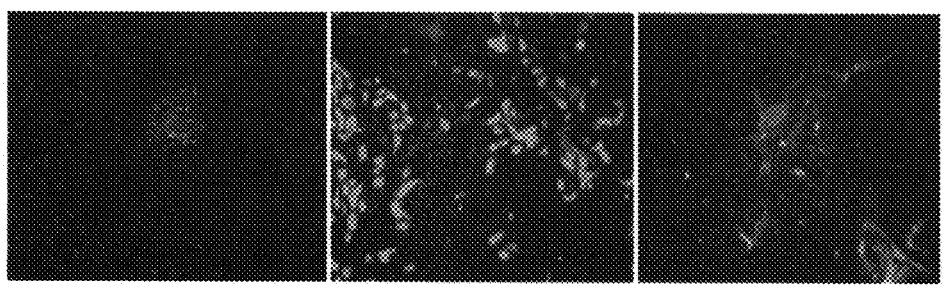
Figures 3G, 3H, 3I:
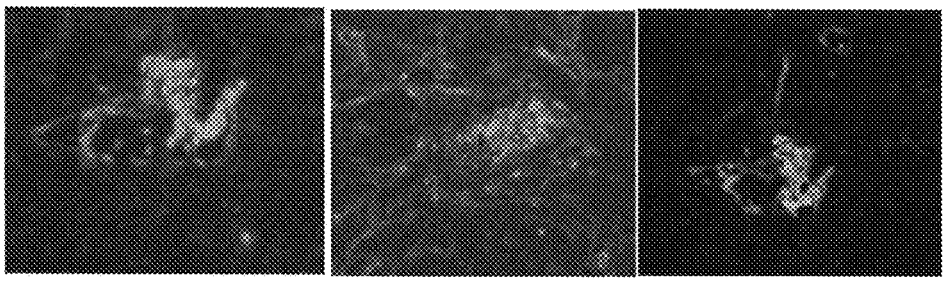

FIGS. 1A-C are photographs illustrating how scaffolds support pancreatic cells in 3D tissue-like structures. (FIG. 1A) Pancreatic Islets scaffold. (FIG. 1B) Histological examination with H&E stain of pancreatic islet grown on 3D polymer scaffold. (FIG. 3C) 3D Co-culture of mouse pancreatic islets fibroblasts and HUVEC on PLLA-PLGA scaffold; 21 days after incubation. Fluorescent staining for Insulin (green) and VWF (red).

FIGS. 2A-B are photomicrographs illustrating mouse pancreatic islets grown on 3D PLLA-PLGA scaffold in the presence (FIG. 2B) and absence (FIG. 2A) of fibroblasts and HUVEC. FIG. 2A illustrates the state of the islets 8 days following incubation. FIG. 2B illustrates the state of the islets following 8 days of incubation. Tissue construct sections were stained using anti VWF (red), anti insulin (green) and DAPI for nuclear staining (blue).

Figures 3J, 3K, 3L:

FIGS. 3A-L are photomicrographs (×10) of co-cultures of mouse pancreatic islets and HUVEC (ECs) stained for insulin (green) and VWF (red) for 8 days (FIGS. 3A-C and 3G-I), for 14 days (FIGS. 3D-F) and 21 days (FIGS. 3J-L). In 3D constructs (FIGS. 3G-L), cells were embedded and sectioned before staining. Note that in 2D cultures (FIGS. 3A-F), endothelial cells organized in clusters and rings, whereas in 3D cultures on the scaffolds they formed into endothelial tubes, in vessel-like networks and allow the longer survival time of the islets and expression of insulin (even after 21 days).

Figure 4:
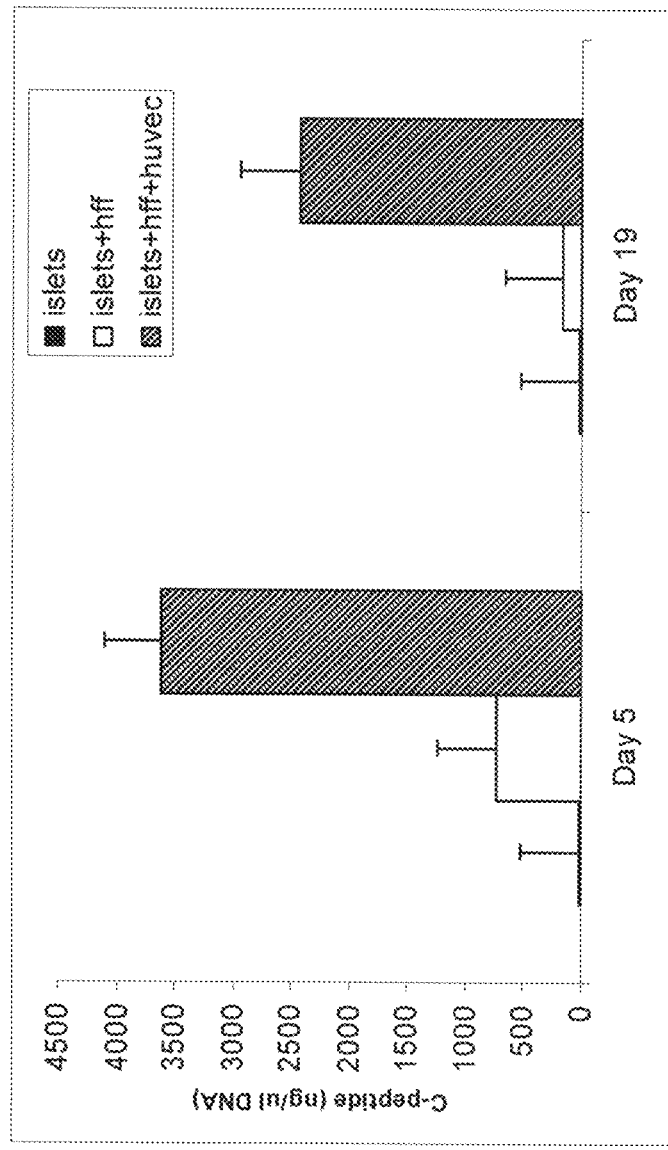

FIG. 4 is a bar graph illustrating the amount of C-Peptide detected in KRB media containing 17.5 mM glucose from 3D scaffold seeded islets.

Figures 5A, 5B:
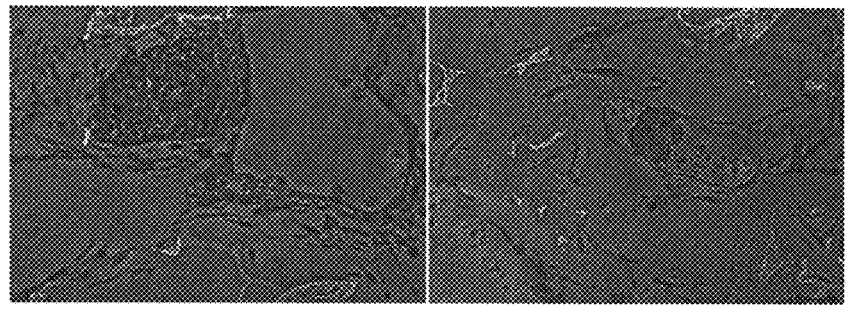
Figures 5C, 5D:
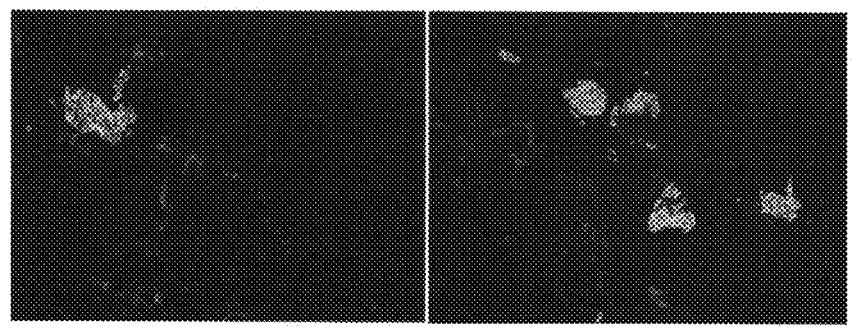
Figures 5E, 5F:
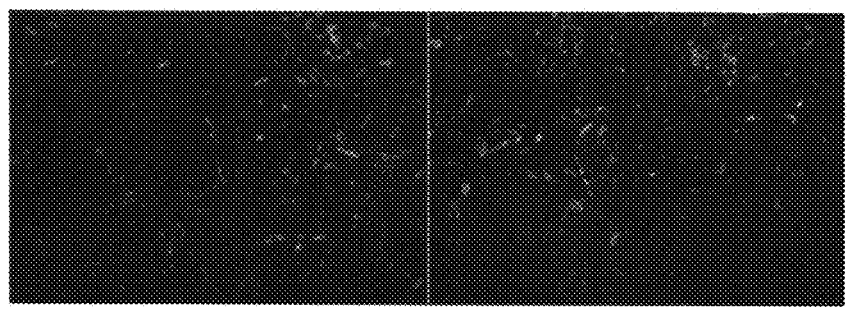

FIGS. 5A-F are photomicrographs of co-cultures of mouse pancreatic islets, foreskin fibroblasts and endothelial cells co-seeded on a 3D polymer scaffold 10 days following implantation (FIGS. 5A-E) and 14 days post implantation (FIG. 5F). FIGS. 5A-B:H&E. FIGS. 5C-D: Double immunofluorescence analysis for anti VWF (red), anti insulin (green). FIGS. 5E-F illustrate that a human vessel-like network integrates with the implanted mouse endothelial cells. Double immunofluorescence analysis for anti VWF (red), anti isolectin-B4 (green) and DAPI (blue).

DESCRIPTION OF THE PREFERRED EMBODIMENTS

The present invention is of scaffold-supported vascularized islets. Specifically, the present invention can be used as a therapeutic following transplantation into a diabetic patient.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In the development of alternative therapeutic strategies for treating diabetes, the transplant of insulin-producing cells continues to attract considerable attention. However, as of yet, these transplants have only met with a limited success rate. It has been suggested that a primary reason for non-immune islet transplantation failure may be the result of angiogenic inefficiency. Beta cells (the insulin producing cells) are located in the central portion of the islet and are thus particularly susceptible to ischemia. Although pancreatic islets in the native pancreas are highly vascularized, islet isolation (prior to islet transplantation) severs arterial and venous connections. These connections must be reestablished for the transplanted islets to survive.

Whilst reducing the present invention to practice, the present inventors have discovered that under appropriate conditions, the seeding of islets on a scaffold in the presence of endothelial cells promotes establishment of 3D endothelial tube structures (FIG. 1C). Furthermore, the present inventors have shown that scaffold-seeded islets and endothelial cells promote functional vascularization. This is evidenced by the data showing that scaffold seeded islets in the presence of endothelial cells, comprise beta cells of an increased viability and of an increased capability for insulin secretion (FIGS. 3A-L) and further secreted greater amounts of c-peptide following glucose stimulation (FIG. 4). Thus for example, islets supported by 3D endothelial structures were able to remain intact and secrete insulin at 21 days (three weeks) post culture, whilst islets supported by 2D endothelial structures were not intact at 21 days and were only able to secrete insulin up to 14 days post culture. In vivo results showed that the scaffold supported islets were capable of expressing and storing insulin for at least 10 days post implantation (FIGS. 5A-F).

U.S. Patent Application No. 20030113302 teaches a method for enhancing vascularization of islets by contact thereof with endothelial cells in the presence or absence of a scaffold. However, U.S. Patent Application No. 20030113302 does not teach transplantation of preformed vascular beds or other vascular structures, either separately or within the scaffold. In fact the above mentioned Application teaches away from transplantation of pre-vascularized islets, since according to the applicants thereof this would be too time-consuming and impractical.

In sharp contrast, the present inventors postulate that transplantation of a pre-vascularized islet would be highly advantageous over transplantation of non-vascularized islet since it would provide the transplanted islets with a "head-start" in the race for survival.

Thus, according to one aspect of the present invention, there is provided a method of ex vivo vascularizing an islet, the method comprising culturing a scaffold-supported islet and endothelial cells under conditions which allow the formation of at least one 3D endothelial structure within said scaffold, thereby ex vivo vascularizing the islet.

As used herein, the phrase "vascularizing an islet" refers to formation of at least a part of a 3D blood vessel network around an islet. Typically, the blood vessel network is comprised of endothelial cells. The vasculature may be at any stage of formation as long as it comprises at least one 3D endothelial structure. Examples of 3D endothelial structures include, but are not limited to tube-like structures, preferable those comprising a lumen.

The term "islet" as used herein refers to pancreatic islets of Langerhans. Islets are made up of two major cell types: the alpha cells, which make glucagon, a hormone that raises the level of glucose (sugar) in the blood, and the beta cells, which make insulin. Within the human pancreas organ there are about 1-1.5 million islets of Langerhans. The islets make up about 2% of the mass of the pancreas, and each islet contains between 2,000 and 10,000 cells.

According to this aspect of the present invention, the islets may or may not be intact. Thus, the present invention also anticipates the use of tissue-engineered constructs comprising islet cells such as beta cells or stem cells differentiated towards a beta cell lineage. Just as with intact islets, it is important to promote microvascularization of the construct to enable the insulin secreted from the beta cells to enter the general circulation, and also to provide the beta cells with a source of oxygen and other nutrients.

Methods of isolating islets are well known in the art. For example, islets may be isolated from pancreatic tissue using collagenase and ficoll gradients. An exemplary method is described in Example 1 herein below. Typically, the islets are isolated from mammals, preferably humans.

As mentioned herein above, the method of the present invention is effected by co-seeding islets and endothelial cells on a scaffold.

The endothelial cells may be human embryonic stem cell (hESC)-derived endothelial cells (Levenberg, et al., Proc Natl Acad Sci USA (2002) 99, 4391-4396, the contents of which are incorporated by reference herein), or primary endothelial cells cultured from e.g. human umbilical vein (HUVEC), or biopsy-derived endothelial cells such as from the aorta or umbilical artery. The endothelial cells of the present invention may also be derived from humans (either autologous or non-autologous) e.g. from the blood or bone marrow. In addition the endothelial cells may be derived from other mammals, for example, humans, mice or cows. For example, endothelial cells may be retrieved from bovine aortic tissue.

In one embodiment, human embryonic endothelial cells are produced by culturing human embryonic stem cells in the absence of LIF and bFGF to stimulate formation of embryonic bodies, and isolating PECAM1 positive cells from the population. HUVEC may be isolated from tissue according to methods known to those skilled in the art or purchased from cell culture laboratories such as Cambrex Biosciences or Cell Essentials.

As used herein, the term "scaffold" refers to a 3 dimensional matrix upon which cells may be cultured (i.e., survive and preferably proliferate for a predetermined time period).

The scaffold of the present invention may be made uniformly of a single polymer, co-polymer or blend thereof. However, it is also possible to form a scaffold according to the invention of a plurality of different polymers. There are no particular limitations to the number or arrangement of polymers used in forming the scaffold. Any combination which is biocompatible, may be formed into fibers, and degrades at a suitable rate, may be used.

Both the choice of polymer and the ratio of polymers in a co-polymer may be adjusted to optimize the stiffness of the scaffold. The molecular weight and cross-link density of the scaffold may also be regulated to control both the mechanical properties of the scaffold and the degradation rate (for degradable scaffolds). The mechanical properties may also be optimized to mimic those of the tissue at the implant site. The shape and size of the final scaffold should be adapted for the implant site and tissue type.

Scaffold material may comprise natural or synthetic organic polymers that can be gelled, or polymerized or solidified (e.g., by aggregation, coagulation, hydrophobic interactions, or cross-linking) into a 3-D open-lattice structure that entraps water or other molecules, e.g., to form a hydrogel. Structural scaffold materials may comprise a single polymer or a mixture of two or more polymers in a single composition. Additionally, two or more structural scaffold materials may be co-deposited so as to form a polymeric mixture at the site of deposition. Polymers used in scaffold material compositions may be biocompatible, biodegradable and/or bioerodible and may act as adhesive substrates for cells. In exemplary embodiments, structural scaffold materials are easy to process into complex shapes and have a rigidity and mechanical strength suitable to maintain the desired shape under in vivo conditions.

In certain embodiments, the structural scaffold materials may be non-resorbing or non-biodegradable polymers or materials.

The phrase "non-biodegradable polymer", as used herein, refers to a polymer or polymers which at least substantially (i.e. more than 50%) do not degrade or erode in vivo. The terms "non-biodegradable" and "non-resorbing" are equivalent and are used interchangeably herein.

Such non-resorbing scaffold materials may be used to fabricate materials which are designed for long term or permanent implantation into a host organism. In exemplary embodiments, non-biodegradable structural scaffold materials may be biocompatible. Examples of biocompatible non-biodegradable polymers which are useful as scaffold materials include, but are not limited to, polyethylenes, polyvinyl chlorides, polyamides such as nylons, polyesters, rayons, polypropylenes, polyacrylonitriles, acrylics, polyisoprenes, polybutadienes and polybutadiene-polyisoprene copolymers, neoprenes and nitrile rubbers, polyisobutylenes, olefinic rubbers such as ethylene-propylene rubbers, ethylene-propylene-diene monomer rubbers, and polyurethane elastomers, silicone rubbers, fluoroelastomers and fluorosilicone rubbers, homopolymers and copolymers of vinyl acetates such as ethylene vinyl acetate copolymer, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyvinylpyrrolidones, polyacrylonitrile butadienes, polycarbonates, polyamides, fluoropolymers such as polytetrafluoroethylene and polyvinyl fluoride, polystyrenes, homopolymers and copolymers of styrene acrylonitrile, cellulose acetates, homopolymers and copolymers of acrylonitrile butadiene styrene, polymethylpentenes, polysulfones, polyesters, polyimides, polyisobutylenes, polymethylstyrenes, and other similar compounds known to those skilled in the art.

In other embodiments, the structural scaffold materials may be a "bioerodible" or "biodegradable" polymer or material.

The phrase "biodegradable polymer" as used herein, refers to a polymer or polymers which degrade in vivo, and wherein erosion of the polymer or polymers over time occurs concurrent with or subsequent to release of the islets. The terms "biodegradable" and "bioerodible" are equivalent and are used interchangeably herein.

Such bioerodible or biodegradable scaffold materials may be used to fabricate temporary structures. In exemplary embodiments, biodegradable or bioerodible structural scaffold materials may be biocompatible. Examples of biocompatible biodegradable polymers which are useful as scaffold materials include, but are not limited to, polylactic acid, polyglycolic acid, polycaprolactone, and copolymers thereof, polyesters such as polyglycolides, polyanhydrides, polyacrylates, polyalkyl cyanoacrylates such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, polyanhydrides, biopolymers such as collagens and elastin, alginates, chitosans, glycosaminoglycans, and mixtures of such polymers. In still other embodiments, a mixture of non-biodegradable and bioerodible and/or biodegradable scaffold materials may be used to form a biomimetic structure of which part is permanent and part is temporary.

PLA, PGA and PLA/PGA copolymers are particularly useful for forming the scaffolds of the present invention. PLA polymers are usually prepared from the cyclic esters of lactic acids. Both L(+) and D(-) forms of lactic acid can be used to prepare the PLA polymers, as well as the optically inactive DL-lactic acid mixture of D(-) and L(+) lactic acids. PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. The erosion of the polyester scaffold is related to the molecular weights. The higher molecular weights, weight average molecular weights of 90,000 or higher, result in polymer scaffolds which retain their structural integrity for longer periods of time; while lower molecular weights, weight average molecular weights of 30,000 or less, result in both slower release and shorter scaffold lives. For example, poly(lactide-co-glycolide) (50:50) degrades in about six weeks following implantation.

According to a preferred embodiment of this aspect of the present invention the scaffold comprises a 50:50 mixture of poly(L-lactic acid) and poly(lactic acid-co-glycolic acid.

In certain embodiments, the structural scaffold material composition is solidified or set upon exposure to a certain temperature; by interaction with ions, e.g., copper, calcium, aluminum, magnesium, strontium, barium, tin, and di-, tri- or tetra-functional organic cations, low molecular weight dicarboxylate ions, sulfate ions, and carbonate ions; upon a change in pH; or upon exposure to radiation, e.g., ultraviolet or visible light. In an exemplary embodiment, the structural scaffold material is set or solidified upon exposure to the body temperature of a mammal, e.g., a human being. The scaffold material composition can be further stabilized by cross-linking with a polyion.

In an exemplary embodiment, scaffold materials may comprise naturally occurring substances, such as, fibrinogen, fibrin, thrombin, chitosan, collagen, alginate, poly(N-isopropylacrylamide), hyaluronate, albumin, collagen, synthetic polyamino acids, prolamines, polysaccharides such as alginate, heparin, and other naturally occurring biodegradable polymers of sugar units.

In certain embodiments, structural scaffold materials may be ionic hydrogels, for example, ionic polysaccharides, such as alginates or chitosan. Ionic hydrogels may be produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix. In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole). Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years or in less than about one year, once exposed to a physiological solution of pH 6-8 having a temperature of between about 25.degree. C. and 38.degree. C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Typically, the scaffolds of the present invention are porous. The porosity of the scaffold may be controlled by a variety of techniques known to those skilled in the art. The minimum pore size and degree of porosity is dictated by the need to provide enough room for the cells and for nutrients to filter through the scaffold to the cells. The maximum pore size and porosity is limited by the ability of the scaffold to maintain its mechanical stability after seeding. As the porosity is increased, use of polymers having a higher modulus, addition of stiffer polymers as a co-polymer or mixture, or an increase in the cross-link density of the polymer may all be used to increase the stability of the scaffold with respect to cellular contraction.

According to a preferred embodiment of this aspect of the present invention, the scaffold has a minimal average pore diameter of about 300 μm and a maximal average pore diameter of about 800 μm.

The scaffolds may be made by any of a variety of techniques known to those skilled in the art. Salt-leaching, porogens, solid-liquid phase separation (sometimes termed freeze-drying), and phase inversion fabrication may all be used to produce porous scaffolds. Fiber pulling and weaving (see, e.g. Vacanti, et al., (1988) Journal of Pediatric Surgery, 23: 3-9) may be used to produce scaffolds having more aligned polymer threads. Those skilled in the art will recognize that standard polymer processing techniques may be exploited to create polymer scaffolds having a variety of porosities and microstructures.

Scaffold materials are readily available to one of ordinary skill in the art, usually in the form of a solution (suppliers are, for example, BDH, United Kingdom, and Pronova Biomedical Technology a.s. Norway). For a general overview of the selection and preparation of scaffolding materials, see the American National Standards Institute publication No. F2064-00 entitled Standard Guide for Characterization and Testing of Alginates as Starting Materials Intended for Use in Biomedical and Tissue Engineering Medical Products Applications".

Therapeutic compounds or agents that modify cellular activity can also be incorporated (e.g. attached to, coated on, embedded or impregnated) into the scaffold material. Campbell et al (US Patent Application No. 20030125410) which is incorporated by reference as if fully set forth by reference herein, discloses methods for fabrication of 3D scaffolds for stem cell growth, the scaffolds having preformed gradients of therapeutic compounds. The scaffold materials, according to Campbell et al, fall within the category of "bio-inks". Such "bio-inks" are suitable for use with the compositions and methods of the present invention.

Exemplary agents that may be incorporated into the scaffold of the present invention include, but are not limited to those that promote cell adhesion (e.g. fibronectin, integrins), cell colonization, cell proliferation, cell differentiation, cell extravasation and/or cell migration. Thus, for example, the agent may be an amino acid, a small molecule chemical, a peptide, a polypeptide, a protein, a DNA, an RNA, a lipid and/or a proteoglycan.

Proteins that may be incorporated into the scaffolds of the present invention include, but are not limited to extracellular matrix proteins, cell adhesion proteins, growth factors, cytokines, hormones, proteases and protease substrates. Thus, exemplary proteins include vascular endothelial-derived growth factor (VEGF), activin-A, retinoic acid, epidermal growth factor, bone morphogenetic protein, TGFβ, hepatocyte growth factor, platelet-derived growth factor, TGFα, IGF-I and II, hematopoetic growth factors, heparin binding growth factor, peptide growth factors, erythropoietin, interleukins, tumor necrosis factors, interferons, colony stimulating factors, basic and acidic fibroblast growth factors, nerve growth factor (NGF) or muscle morphogenic factor (MMP). The particular growth factor employed should be appropriate to the desired cell activity. The regulatory effects of a large family of growth factors are well known to those skilled in the art.

Seeding of the cells on the scaffolds is also a critical step in the establishment of the vascularized islets of the present invention. Since it has been observed that the initial distribution of cells within the scaffold after seeding is related to the cell densities subsequently achieved, methods of cell seeding require careful consideration. Thus, cells can be seeded in a scaffold by static loading, or, more preferably, by seeding in stirred flask bioreactors (scaffold is typically suspended from a solid support), in a rotating wall vessel, or using direct perfusion of the cells in medium in a bioreactor. Highest cell density throughout the scaffold is achieved by the latter (direct perfusion) technique. An exemplary seeding procedure is described in Example 1 herein below.

The cells may be seeded directly onto the scaffold, or alternatively, the cells may be mixed with a gel which is then absorbed onto the interior and exterior surfaces of the scaffold and which may fill some of the pores of the scaffold. Capillary forces will retain the gel on the scaffold before hardening, or the gel may be allowed to harden on the scaffold to become more self-supporting. Alternatively, the cells may be combined with a cell support substrate in the form of a gel optionally including extracellular matrix components. An exemplary gel is Matrigel™, from Becton-Dickinson. Matrigel™ is a solubilized basement membrane matrix extracted from the EHS mouse tumor (Kleinman, H. K., et al., Biochem. 25:312, 1986). The primary components of the matrix are laminin, collagen I, entactin, and heparan sulfate proteoglycan (perlecan) (Vukicevic, S., et al., Exp. Cell Res. 202:1, 1992). Matrigel™ also contains growth factors, matrix metalloproteinases (MMPs [collagenases]), and other proteinases (plasminogen activators [PAs]) (Mackay, A. R., et al., BioTechniques 15:1048, 1993). The matrix also includes several undefined compounds (Kleinman, H. K., et al., Biochem. 25:312, 1986; McGuire, P. G. and Seeds, N. W., J. Cell. Biochem. 40:215, 1989), but it does not contain any detectable levels of tissue inhibitors of metalloproteinases (TIMPs) (Mackay, A. R., et al., BioTechniques 15:1048, 1993). Alternatively, the gel may be growth-factor reduced Matrigel, produced by removing most of the growth factors from the gel (see Taub, et al., Proc. Natl. Acad. Sci. USA (1990); 87 (10:4002-6). In another embodiment, the gel may be a collagen I gel, alginate, or agar. Such a gel may also include other extracellular matrix components, such as glycosaminoglycans, fibrin, fibronectin, proteoglycans, and glycoproteins. The gel may also include basement membrane components such as collagen IV and laminin. Enzymes such as proteinases and collagenases may be added to the gel, as may cell response modifiers such as growth factors and chemotactic agents.

As mentioned above, the method of the present invention is effected by culturing a scaffold-supported islet and endothelial cells under conditions which allow the formation of at least one 3D endothelial structure within the scaffold.

The present inventors have shown that one of these conditions comprises seeding the above mentioned cells in a medium which supports both endothelial tube structures as well as pancreatic tissue survival. An exemplary medium with these attributes is one which comprises a 50% endothelial medium (e.g. EGM2, Cambrex) and a 50% islet medium (e.g. CMRL-1066, Biological industries).

Another of these conditions comprises culturing for a sufficient time following initial seeding on the scaffold for the formation of a 3D endothelial structure. The present inventors have shown that a period of at least 1 week, more preferably 10 days and even more preferably two weeks is required for the formation of such structures.

The present inventors have shown that promotion of 3D endothelial structures may also be enhanced by addition of fibroblast cells (e.g. mouse embryonic fibroblasts or human embryonic fibroblasts). Fibroblasts may be isolated from tissue according to methods known to those skilled in the art (e.g. obtained from E-13 ICR embryos) or purchased from cell culture laboratories such as Cambrex Biosciences or Cell Essentials.

Accordingly, compositions obtained according to the methods describe herein typically comprise a heterogenous population of cells, including, but not limited to pancreatic islet cells, (beta cells and alpha cells), endothelial cells and fibroblast cells.

Since the compositions of the present invention comprise cells that are capable of storing and secreting insulin, they may be used for treating a disease which is associated with insulin deficiency such as diabetes.

Thus, according to another aspect of the present invention there is provided a method of treating diabetes in a subject, the method comprising transplanting a therapeutically effective amount of the compositions of the present invention into the subject, thereby treating diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the scaffold supported cells of the present invention, using any suitable route. Typically, the scaffold supported cells may be administered by injection using a catheter into the portal vein of the liver, underneath the kidney capsule, although other methods of administration are envisaged. For example, Dufour et al., [Tissue engineering, September 2005, Vol. 11, No. 9-10: 1323-1331] successfully administered scaffold supported cells in the epididymal fat pad of diabetic mice.

Any of the cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Pollok et al were able to successfully encapsulate a polymer scaffold seeded with islets using porcine chondrocytes [Dig Surg 2001; 18:204-210].

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J. Microencapsul. 2000, 17:245-51.

For example, microcapsules may be prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The scaffold supported cells of the present invention may be transplanted to a human subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the scaffold supported cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (insulin producing cells) effective to prevent, alleviate or ameliorate symptoms of a disorder (e.g., diabetes) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

Example 1

Generation of 3D Pancreatic Islet Co-Culture System

Materials and Methods

Animals: 3 month old C57 black male mice.

Isolation of mouse pancreatic islets: Adult pancreatic islets were isolated from mice pancreases by using collagenase P (Roche). Briefly, the bile duct was clamped off at its duodenal insertion by using a small bulldog clamp. A total of 5 ml 1.5 mg/ml collagenase was injected into the bile duct, followed by digestion at 37° C. for 15 min. After two centrifugations, islets were handpicked under a stereomicroscope.

Cell culture: 10-30 mouse pancreatic islets were cultured on PLLA/PLGA scaffold (PLGA, Boehringer Ingelheim Resomer 503H, Ingelheim, Germany, $M_n \approx 25,000$ and PLLA, Polysciences, Warrington, Pa., $M_n \approx 300,000$) in the presence and absence of fibroblasts and HUVEC for up to three weeks following which they were fixed and embedded in formalin.

Medium conditions: First co-culture medium conditions were identified—a medium in which the different cells can be grown together. Preliminary results with adult islets suggested that a 50% endothelial medium (EGM2, Cambrex) and 50% islet medium (CMRL-1066, Biological industries) could promote endothelial tube structures as well as pancreatic tissue survival.

Seeding procedure: For cell seeding, the scaffolds were cut into rectangular pieces of 5×4×1 mm$^3$ and sterilized. Co-culture of endothelial cells and pancreatic islets was first generated by resuspending an amount of $10^6$ endothelial cells per each scaffold in 15 μl culture medium. For tri-culture systems 30,000 human foreskin fibroblasts were added to the above described co-culture. The cell suspension was seeded on the biodegradable PLLA/PLGA scaffolds (about 1-2 million cells were seeded per 5×5×1 $mm^3$). Scaffolds with cells were cultured for 1-3 weeks on an orbital shaker, to allow better medium perfusion and prevent attachment of the scaffolds to the plate. To facilitate cell attachment to the scaffolds, two methods were used:

(1) Seeding the cells onto the scaffold with matrigel: prior to seeding, the cells were resuspended in 15 μl of a 1:1 mixture of culture medium and growth factor-reduced Matrigel (BD Biosciences).

(2) Coating the scaffold with fibronectin: scaffolds were soaked in 50 μg/mL of fibronectin (Sigma) for 1 hour and washed in PBS prior to direct cell seeding (without matrigel) in 15 μL of media.

Staining of islets: Islets grown on tissue culture plates were fixed in 3.2% paraformaldehyde (PFA)+0.5% triton for 5 min at room temperature (RT) followed by 25 min of fixation in 3.2% PFA. For histological analysis the scaffolds were fixed in 4% PFA for 6 hours at RT before paraffin embedding. Transverse Paraffin sections of 5 μm were cut with a microtome and placed on slides for immunohistochemistry or staining with hematoxylin and eosin (H&E) and store at RT. Paraffin sections were dewaxed in 60° C. oven for 30 min. Antigen retrieval was accomplished by reveal treatment (Biocare Medical) for 20 min in 95° C. cloaking chamber (Biocare Medical), followed by two washes in distilled water (DW) and blocked with 10% FCS serum for 10 min. After blocking of non-specific binding, the primary antibodies were applied at the proper concentrations: rabbit anti-human vWF (1:1000), guinea-pig anti-insulin (1:200), (Dako), for 30 min at RT followed by two washes in PBS. Sections were then incubated with the secondary antibodies, Cy3-labeled goat anti-mouse IgG, Cy3-labeled donkey anti-rabbit, Cy2-labeled donkey anti-guinea-pig IgG (Jackson ImmunoResearch) and AlexaFluor goat anti-rabbit IgG (Molecular Probes) together with with 4',6-diamidino-2-phenylindole (DAPI). After immunolabeling, cells were mounted in Floromount-G (Southern Biotechnology) and were examined with a conventional fluorescence microscope (Zeiss).

Results

FIG. 1A illustrates a typical PLLA/PLGA biodegradable polymeric scaffold. Sections stained with H&E indicated islets attached to the scaffolds (FIG. 1B). Upon addition of endothelial cells to the culture, vessel networks formed around and sometimes in between the islets (FIG. 1C).

Example 2

Role of Endothelial Cells on Pancreatic Islet Survival

In order to demonstrate the role of endothelial cells on pancreatic islet survival, pancreatic islets were grown with or without endothelial cells.

Materials and Methods

The 3D pancreatic islet co-culture system was generated as described for Example 1.

Results

Without endothelial cells, the islets deteriorated following 8 days in culture, as can be clearly seen in FIG. 2A. However in islets co-cultured with endothelial cells the islets remained intact and express high levels of insulin even after 21 days (FIGS. 3J-L).

These preliminary results exhibit the important role of endothelial cells in preserving the morphology and survival of the islets cells.

Example 3

Role of 3D Microenvironment on Pancreatic Islet Survival

To emphasize the role of 3D microenvironment, the identical cell cultures as in Example 2 were grown on tissue plates, a 2D setting.

Materials and Methods

The 3D pancreatic islet co-culture system was generated as described for Example 1.

The 2D pancreatic islet co-culture system was generated essentially as above using 6 well tissue plates (Nunc A/S).

Results

The endothelial organization was profoundly different in the 3D and 2D culture settings (FIGS. 3A-L).

Round clusters and rings were observed in the 2D culture, while the 3D allowed the cells to form elongated interconnecting tubes, forming a vascular network-like structure. Following 8 or 21 days the different cultures were fixed and embedded. Sections were stained for VWF (endothelial marker), and Insulin.

Conclusions

The results herein show the importance of a 3D culture system. The presence of endothelial cells forming 3D vessel-like structures was found critical for islet survival. In 3D cultures even following 21 days the islets remained intact and expressed insulin. In sharp contrast, in 2D cultures the islets broke down and did not express insulin from day 14 of culture. Dramatic differences were also found between islets cultures with endothelial cells (intact and insulin expressing after 8 days and 3 weeks) and cultures without endothelial cells or without direct contact with the endothelial cells. Based on previous reports eluding to the critical role of 3D organization on cellular interactions and signaling, it is anticipated that endothelial tubes in a 3D environment provide a signal which might not be available in 2D co-culture setting.

Example 4

In Vitro Function of Vascularized Pancreatic Islets

To study the therapeutic potential of the pancreatic 3D constructs, glucose tolerance tests were performed at different time points following seeding of the islets and cells on the scaffolds.

Materials and Methods

Glucose tolerance tests were performed on (1) scaffold seeded pancreatic islets; (2) scaffold seeded pancreatic islets and foreskin fibroblasts (hff); and (3) scaffold seeded pancreatic islets, foreskin fibroblasts (hff) and endothelial cells (huvec). The tests were performed 5 and 19 days post scaffold seeding.

Results

The results show that addition of endothelial cells significantly inducted c-peptide secretion in response to glucose compared to control constructs of islets alone or islets with fibroblasts only (FIG. 4).

Example 5

In Vivo Survival and Function of Vascularized Pancreatic Islets

Materials and Methods

Vascularized islet constructs of the present invention were implanted subcutaneously in the back of SCID mice and retrieved following 2-3 weeks. The islets were stained using H&E.

Results

H&E staining of construct sections revealed that the islets are intact and surrounded by supporting tissue and vessel structures (FIG. 5A-B). In vivo, the islets continued to express and store high levels of insulin as shown by immunofluorescent staining. Interestingly, human vessels (VWF positive, isolectin-4 negative) originating from the implanted construct-derived HUVEC cells were shown to be in close proximity to the islets. These cells were gradually replaced by mice endothelial cells (isolectin-4 positive) invading and vascularizing the constructs (FIG. 5C-F).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of ex vivo vascularizing a pancreatic islet, the method comprising co-seeding pancreatic islets, fibroblast cells and endothelial cells on a porous scaffold under conditions which allow the formation of a network of vasculature within said scaffold, wherein a pore of said porous scaffold is between 300 µm-800 µm, thereby ex vivo vascularizing the pancreatic islet.

2. The method of claim 1, wherein said conditions comprise an ex vivo culturing period of at least 1 week.

3. The method of claim 1, further comprising resuspending said endothelial cells prior to said co-seeding.

* * * * *